United States Patent [19]

Blair et al.

[11] 4,266,035

[45] May 5, 1981

[54] PROCESS FOR DECOLORIZING PULP AND PAPER MILL WASTEWATER AND MICROORGANISM CAPABLE OF SAME

[75] Inventors: James E. Blair, Roanoke; Lois T. Davis, Salem, both of Va.

[73] Assignee: Sybron Corporation, Rochester, N.Y.

[21] Appl. No.: 51,296

[22] Filed: Jun. 22, 1979

Related U.S. Application Data

[62] Division of Ser. No. 8,215, Jan. 31, 1979, Pat. No. 4,199,444.

[51] Int. Cl.³ .............................................. C12N 1/20
[52] U.S. Cl. ..................................... 435/253; 435/875
[58] Field of Search ................................. 435/253, 875

[56] References Cited

U.S. PATENT DOCUMENTS

| | | | |
|---|---|---|---|
| 3,816,260 | 6/1974 | Sugiyama | 435/253 X |
| 3,843,517 | 10/1974 | McKinney et al. | 435/875 X |

*Primary Examiner*—Thomas G. Wyse
*Attorney, Agent, or Firm*—Sughrue, Rothwell, Mion, Zinn and Macpeak

[57] ABSTRACT

A process of decolorizing pulp and paper mill wastewater comprising treating wastewater effluent from a pulp or paper mill with a novel microbial strain of *Pseudomonas aeruginosa* under aerobic conditions; and the novel microorganism of the strain *Pseudomonas aeruginosa*.

1 Claim, No Drawings

PROCESS FOR DECOLORIZING PULP AND PAPER MILL WASTEWATER AND MICROORGANISM CAPABLE OF SAME

This is a division of application Ser. No. 8,215, filed Jan. 31, 1979 now U.S. Pat. No. 4,199,444.

BACKGROUND OF THE INVENTION

1. Field Of The Invention

This invention relates to a process of decolorizing pulp and paper mill wastewater and, more specifically, to a process for treating wastewater effluent from a pulp or paper mill with a novel microorganism of the strain *Pseudomonas aeruginosa* whereby color bodies in the pulp and paper wastewater are thereby removed and the wastewater is decolorized. Further, this invention relates to a novel microbial strain of the genus Psuedomonas.

2. Description Of The Prior Art

Pulp and paper mill wastewaters are generally obtained as a result of manufacturing processes for the preparation of wood pulp and paper. Due to the presence of organic and inorganic materials in such wastewaters rendering such wastewaters unsuitable for reuse and undesirable for release into the biosphere due to the pollution problems which result when they are discharged untreated, pulp and paper mill wastewaters are generally processed in biological treatment systems, for example, aerated lagoons or activated sludge systems, for removal of biodegradable organic matter prior to reuse or discharge to receiving bodies of water.

While the biological processes occurring during such a biological treatment provide the ability to produce effluent which has both low biological oxygen demand (BOD) and low chemical oxygen demand (COD), unfortunately, conventionally employed biological treatment systems accomplish very little, if any, reduction in color of the pulp and paper mill wastewater when the pulp and paper wastewater is so treated. For example, trickling filters have been recommended by governmental environmental regulatory agencies for use in processing wastewater effluent from pulp and paper mills. However, no color removal has been achieved (see H. T. Chen et al., "Four Biological Systems for Treating Integrated Paper Mill Effluent," *TAPPI*, 57, 5 (111-115) (1974)).

Also, a system comprising plastic disks on a single shaft which is rotated (as disclosed in D. J. Bennett et al., "Pilot Application of the Rotating Biological Surface Concept for Secondary Treatment of Insulating Board Mill Effluents," *TAPPI*, 56, 12 (182-187) (1973)) and an activated sludge treatment using oxygen instead of air (as disclosed in R. J. Grader et al., "The Activated Sludge Process Using High-Purity for Treating Kraft Mill Wastewater," *TAPPI*, 56, 4 (103-107) (1973)) have been used, but no reduction in color of paper mill waste has been reported using either system. In some instances, it has been observed that an increase in true color in actuality occurs.

From this observed result, it is apparent that the aerobic bacteria typically present in such treatment systems are not capable of utilizing the color bodies which are present in the wastewater from pulp and paper processing as a source of food. Even with the well-known ability and adaptability of bacteria to adjust to and utilize new substrates as food sources, thus far the development of bacteria capable of reducing color in pulp and paper mill wastewater effluent has not been reported.

Whereas regulatory guidelines for paper mill waste color have not been set forth, much work has been done to evaluate the various physical-chemical methods for removing color, such as lime precipitation, resin separation, activated carbon adsorption, and ozonation, all with varied degrees of success and in all cases involving high cost for initial capital equipment and ongoing operating and maintenance expenditures. Refer to review article for chemical physical methods, "Current Status of the Effluent Decolorization Problem," by Isiah Gellman and Herbert F. Berger. *TAPPI*, Volume 57, No. 9 (September 1974).

With the increasing concern as to minimization of the problems arising from pollution, biological processes utilizing microorganisms are being industrially employed in an increasing amount, and a large amount of activity in research and development is occurring presently to develop new microbial strains capable of use in wastewater treatment both industrially and domestically. Even with this increased activity in investigating and developing strains of microorganisms to solve particular waste removal problems, no reduction in color which exists in effluent wastewater from pulp and paper mills has been achieved.

In the past, *Polyporus versicolor* has been used to degrade color bodies in paper mill effluent, but such was in the presence of carbohydrates. However, no significant reduction was seen in the absence of carbohydrates (e.g., as disclosed in Marton and Stern, "Decolorization of Kraft Black Liquor with *Polyporus versicolor*, a White Rot Fungus," *TAPPI*, 52, 10 (1969)). Furthermore, filamentous organisms such as *Polyporus versicolor* are impractical for use in biological treatment systems.

SUMMARY OF THE INVENTION

Accordingly, an object of this invention is to provide a process whereby pulp and paper mill wastewater effluent can be decolorized.

Another object of this invention is to provide a biological process for treatment of pulp and paper mill wastewater effluent to not only remove biodegradable organic matter therefrom but to specifically reduce or decolorize pulp and paper mill wastewater.

A further object of this invention is to provide a biological treating process for decolorizing pulp and paper mill wastewater using a novel mutant strain of *Pseudomonas aeruginosa*.

An even further object of this invention is to provide a biological treatment process of pulp and paper mill wastewater to decolorize the same and render such suitable for discharge into the biosphere, thereby minimizing problems of pollution.

Also, an object of this invention is to provide a biological treatment process of pulp and paper mill wastewater to decolorize the same using a novel mutant microorganism which does not require the addition of carbohydrates to the system and which is well adapted to biological treatment systems.

An additional object of this invention is to provide a novel mutant strain of the species *Pseudomonas aeruginosa*.

In one embodiment of this invention, this invention provides a process of decolorizing pulp and paper mill wastewater which comprises treating wastewater effluent from a pulp or paper mill with a microorganism of the strain *Pseudomonas aeruginosa* 4-5-14.

DETAILED DESCRIPTION OF THE INVENTION

In another embodiment of this invention, this invention provides a novel strain of the species *Pseudomonas aeruginosa* 4-5-14 having the characteristics described below.

The novel mutant *Pseudomonas aeruginosa* 4-5-14 (hereinafter "mutant strain") was produced by mutation of a parent strain of *Pseudomonas aeruginosa* isolated from the soil surrounding a pulp and paper mill wastewater lagoon at a large Kraft paper mill located in Franklin, Va.

This novel mutant strain has been found to be capable of decolorizing pulp and paper mill wastewater and has the characteristics described below.

The mutant strain *Pseudomonas aeruginosa* 4-5-14 is a gram-negative, non-spore-forming rod. The cells are straight rods which have a single-polar flagellum, and the cells are motile. In culture, approximately 1% of the cells exist in the form of long filaments of greater than five cell units long. On Kings Medium A (described in E. O. King et al., *J. Lab. & Clin. Med.*, Volume 44, No. 2, page 303 (1954), and on Difco BACTO-Antibiotic Medium 3 (trade name produced by Difco Laboratories), solidified with agar at temperatures from 20°–40° C., a blue-green diffusible pigment is formed. A characteristic grape-like odor is given off by cultures of *Pseudomonas aeruginosa* 4-5-14 on complex media such as nutrient broth and nutrient agar, and on minimal salts-based media containing a carbon source such as glucose.

The mutant strain *Pseudomonas aeruginosa* 4-5-14 is capable of growing on either a glucose or acetate containing minimal salts medium (Roy Curtiss, III, *J. Bact.*, 89, pages 28–40 (1965)) containing ammonium ion as a nitrogen source, thus demonstrating the strain does not appear to require any growth factor or vitamin supplement.

The mutant strain is an obligate aerobe, although growth is possible anaerobically in the presence of nitrate, in which case a gas is formed. On metabolism in the presence of nitrate, the mutant strain produces nitrate reductase. The cells of the mutant strain are incapable of accumulating poly-β-hydroxybutyric acid granules even though DL-hydroxybutyrate serves as a sole carbon source.

A suitable growth temperature range is about 20°–41° C., with optimal growth occurring at 37° C. No growth is observed in ten days at 14° C. The strain displays arginine dihydrolase activity and is capable of gelatin hydrolysis.

Other cultural characteristics and colonial morphology of this mutant strain are shown in Tables 1–6 below.

In the following tables, *Pseudomonas aeruginosa* strain PAO (ATCC 13525) was employed as a known type strain for characterization purposes.

TABLE 1

| MICROSCOPIC MORPHOLOGY | | |
|---|---|---|
| | STRAIN | |
| CHARACTERISTIC | PSEUDOMONAS AERUGINOSA** | 4-5-14 |
| Cell Size* | | |
| Length | 1.5–3.0 | 1.5–3.0 |
| Width | 0.5–0.8 | 0.5–0.8 |
| Gram Reaction | Negative rod | Negative |

TABLE 1-continued

| MICROSCOPIC MORPHOLOGY | | |
|---|---|---|
| | STRAIN | |
| CHARACTERISTIC | PSEUDOMONAS AERUGINOSA** | 4-5-14 |
| | | rod |

*Wet mounts of ten-hour cultures (late exponential phase) viewed under phase contrast (1000X). Sizes given in micrometers.
**Data from Bergey's Manual of Determinative Bacteriology, 8th Ed., The Williams & Wilkins Co., Baltimore (1974).

TABLE 2

COLONIAL CHARACTERISTICS OF
*PSEUDOMONAS AERUGINOSA* 4-5-14
(After 48 Hours At 35° C.)

Plate Count Agar
Circular, flat colonies with a wrinkled surface and slightly undulate edge. Colonies are white, transparent and 5–7 mm in diameter. No pigments are produced after 48 hours.

Nutrient Agar
Circular, umbonate colonies with a wrinkled surface and slightly undulate edge. Colorless colonies are transparent with an opaque center and are 5–7 mm in diameter. No pigments are produced.

Hektoen Enteric Agar
Slightly irregular colonies are flat, rough, green, with an undulate edge. These transparent colonies are 3–8 mm in diameter. No pigments are produced.

Pseudosel Agar
Circular, convex colonies are smooth, white, have an entire edge, are opaque, 1–1.5 mm in diameter, and produce a blue-green diffusible fluorescent pigment.

Trypticase Soy Agar
Colonies are circular, slightly umbonate, wrinkled, with a slight undulate edge. They are somewhat transparent, 2–3 mm in diameter, white, and produce a yellow diffusible fluorescent pigment.

NOTE:
Plate Count Agar and Hektoen Enteric Agar are products of Difco Laboratories. Pseudosel Agar, Nutrient Agar and Trypticase Soy Agar are products of Baltimore Biological Laboratories.

TABLE 3

| UTILIZATION OF CARBON-CONTAINING COMPOUNDS FOR GROWTH | | |
|---|---|---|
| | GROWTH RESPONSE** | |
| COMPOUND* | PSEUDOMONAS AERUGINOSA | 4-5-14 |
| Carbohydrates (& Sugar Derivatives) | | |
| α-Cellulose | + | + |
| L-Arabinose | − | − |
| D-Ribose | − | − |
| D-Glucose | + | + |
| Sucrose | − | − |
| Trehalose | − | − |
| D-Cellobiose | − | − |
| Xylose | − | − |
| Organic Acids | | |
| Acetate | | + |
| Propionate | − | − |
| Butyrate | | ± |
| Isobutyrate | − | − |
| Valerate | − | − |
| Caproate | − | − |
| Heptanoate | − | − |
| Caprate | − | − |
| Stearate | + | + |
| Dicarboxylic Acids | | |
| Maleate | + | + |
| Malonate | − | − |
| Succinate | − | − |
| Glutarate | − | − |
| Saccharate | | |

TABLE 3-continued
UTILIZATION OF CARBON-CONTAINING COMPOUNDS FOR GROWTH

| COMPOUND* | GROWTH RESPONSE** PSEUDOMONAS AERUGINOSA | 4-5-14 |
|---|---|---|
| Hydroxyacids | | |
| L-Malate | − | − |
| DLβ-Hydroxybutyrate | | + |
| DL-Lactate | − | − |
| DL-Glycerate | + | + |
| Miscellaneous Organic Acids | | |
| Citrate | − | − |
| α-Ketoglutarate | − | − |
| Pyruvate | + | + |
| Polyhydric Alcohols and Glycols | | |
| Mannitol | + | + |
| Glycerol | + | + |
| Propyleneglycol | | + |
| m-Inositol | | − |
| Sorbitol | | − |
| Alcohols | | |
| Ethanol | | + |
| n-Propanol | + | + |
| n-Butanol | ± | + |
| Non-Nitrogenous Aromatic And Other Cylic Compounds | | |
| Benzoate | − | − |
| Aliphatic Amino Acids | | |
| Lα-Alanine | + | + |
| Dα-Alanine | + | + |
| β-Alanine | | + |
| L-Leucine | + | + |
| L-Aspartate | + | + |
| L-Glutamate | + | + |
| L-Lysine | + | + |
| DL-Arginine | | + |
| L-Valine | | − |
| Glycine | | − |
| Asparagine | + | + |
| Amino Acids And Related Compounds Containing A Ring Structure | | |
| L-Histidine | + | + |
| L-Proline | + | + |
| L-Tyrosine | − | ± |
| Miscellaneous Nitrogenous Compounds | | |
| Betaine | + | + |
| Sarcosine | − | − |
| Acetamide | + | + |
| Glucosamine | − | − |
| Detergents* | | |
| Igepal CO 520 (2000 mg/l) | ± | − |
| Igepal CO 610 (2000 mg/l) | ± | − |
| Igepal CO 660 (2000 mg/l) | ± | − |

*Compound added at 0.5% to minimal salts medium (Curtiss (1965)).
** + indicates growth greater than blank; − indicates growth less than that of blank; ± indicates growth approximately equal to blank or weak growth, after 7 days at 30° C.
***Trade name for a non-ionic nonyl phenol-ethylene oxide condensate produced by GAF.

TABLE 4
UTILIZATION OF NITROGENOUS COMPOUNDS AS SOLE NITROGEN SOURCE

| COMPOUND* | GROWTH RESPONSE** PSEUDOMONAS AERUGINOSA | 4-5-14 |
|---|---|---|
| NH₄Cl | − | − |
| KNO₃ | − | − |
| L-Glutamate | + | + |
| L-Aspartate | − | − |
| L-Alanine | − | ± |

*Compound added at 0.5 g/100 ml to minimal salts medium (Curtiss (1965) but without NH₄Cl and NH₄NO₃) consisting of 0.5 g of D-glucose/100 ml.
** + indicates growth greater than blank; − indicates growth less than that of blank; ± indicates growth approximately equal to blank or weak growth, after 7 days at 30° C.

TABLE 5
CULTURE GROWTH IN PRESENCE OF HEAVY METALS

| HEAVY METAL* | CONCENTRATION | STRAIN RESPONSE** PSEUDOMONAS AERUGINOSA | 4-5-14 |
|---|---|---|---|
| HgSO₄ | $2 \times 10^{-3}$M | − | − |
| | $10^{-3}$M | − | + |
| | $10^{-4}$M | − | + |
| | $10^{-5}$M | + | + |
| CdCl₂ | $2 \times 10^{-3}$M | − | − |
| | $10^{-3}$M | − | − |
| | $10^{-4}$M | + | + |
| | $10^{-5}$M | + | + |
| CoCl₂ | $2 \times 10^{-3}$M | − | − |
| | $10^{-3}$M | − | + |
| | $10^{-4}$M | + | + |
| | $10^{-5}$M | + | + |
| AgSO₄ | $2 \times 10^{-3}$M | − | − |
| | $10^{-3}$M | − | − |
| | $10^{-4}$M | − | − |
| | $10^{-5}$M | − | − |
| Na₂HAsO₄ | $2 \times 10^{-3}$M | − | + |
| | $10^{-3}$M | + | + |
| | $10^{-4}$M | + | + |
| | $10^{-5}$M | + | + |

*Heavy metal added to minimal salts medium containing (0.5%) D-glucose (Curtiss (1965)).
**Growth response scored as: + indicates growth (no inhibition); − indicates no growth (inhibition).

TABLE 6
RESISTANCE TO ANTIBIOTICS

| ANTIBIOTIC | STRAIN GROWTH RESPONSE 4-5-14 |
|---|---|
| Ampicillin | R* |
| Carbenicillin | S |
| Cephalothin | R |
| Chloramphenicol | R |
| Coly-mycin | S |
| Gentamicin | S |
| Kanamycin | R |
| Mandol | R |
| Streptomycin | R |
| Tobramycin | S |
| Tetracycline | R |
| Amikacin | S |

*Growth response on Pfizer Antimicrobial Susceptibility Disks; Pfizer, Inc. scored: S = sensitive to antibiotic; R = resistant to antibiotic; I = intermediate.

On the basis of the morphological, cultural, and physiological characteristics set forth above, the strain has been identified as a member of the species, *Pseudomonas aeruginosa* and has been designated herein as *Pseudomonas aeruginosa* 4-5-14. A culture of the strain has been deposited in the American Type Culture Collection and has received an accession number, ATCC-31482.

As indicated above, the parent strain from which the mutant strain was developed was isolated and grown on solidified agar medium containing Kraft paper mill black liquor waste diluted 50% by volume with water and fortified with 400 mg/l of ammonium sulfate and 80 mg/l of disodium phosphate. A single colony isolate showing the largest diameter and the darkest color indicating adsorption of color bodies was selected.

This isolate was then subjected to a mutagenesis using 0.02% sodium nitrite at a pH of 6.5-6.8 as described by J. H. Miller, *Experiments in Molecular Genetics,* Cold Spring Harbor Laboratory, New York (1972), and ultraviolet treatment (12 in from the ultraviolet light source for 40 sec. at a wavelength of about 2650 Å; ultraviolet light source: Hanovia Lethray Ultraviolet Lamp) in sequence.

An individually treated colony from each isolate was the inoculated into a liquid water solution containing 50% paper mill wastewater fortified with the above-described amounts of ammonium sulfate and disodium phosphate. Subsequently, an assay for color reduction in shake flasks after 3.5 and 5 days was conducted.

The color in each flask was measured before and after the assay period using the NCASI process ("An Investigation of Improved Procedures for Measurement of Mill Effluent and Receiving Water Color," *NCASI Technical Bulletin* #253 (December 1971)).

Isolates from the flask with the highest color removal were obtained and contacted with 8-azaguanine in an amount of 50 ppm in a liquid nutrient medium in shake flasks for 25 hours comprising 1% N-Z amine (hydrolyzed casein), 1% soy peptone, 0.3% D-glucose, 20% paper mill wastewater, with the pH adjusted to 6.8. The organism demonstrating the best color reduction was then grown in the liquid nutrient medium having the composition previously described additionally containing 50 ppm ethyleneimine, a mutagenic agent, for 18-28 hours as required for sufficient growth. This was then streaked onto selective agar, undiluted paper mill wastewater containing, as basic salts, 400 ppm $(NH_4)_2SO_4$ and 80 ppm disodium phosphate, with agar to solidify. The largest colonies were assayed for color reduction and ability to grow in 100% Kraft paper mill black liquor. The colony isolated and found to be the best in terms of growth and decolorization was selected and, as indicated above, was found to be a novel strain of the species *Pseudomonas aeruginosa* and is designated herein as *Pseudomonas aeruginosa* 4-5-14.

The mutant strain *Pseudomonas aeruginosa* 4-5-14 can be employed alone or in combination with other microorganisms conventionally used in microbiological treatment of wastes. This invention also includes the use of any variants of *Pseudomonas aeruginosa* 4-5-14 alone or in combination.

The mutant strain *Pseudomonas aeruginosa* 4-5-14 used in this invention can be cultured in wastewater from a pulp or paper mill either using a batch process, a semi-continuous process or a continuous process, and such is cultured for a time sufficient to degrade the colorant materials present in the wastewater and remove them or break them down into components capable of being degraded by other organisms normally found in biological wastewater treatment systems.

The mutant strain of this invention can be employed in ion exchange resin treatment systems, in trickling filter systems, in carbon adsorption systems, in activated sludge treatment systems, in outdoor lagoons or pools, etc. Basically, all that is necessary is for the microorganism to be placed in a situation of contact with the wastewater effluent from a pulp or paper mill. In order to degrade the material present in the wastewater, the organism can be cultured at conditions of about 15° C. to about 40° C., preferably about 18° C. to about 37° C. Desirably, the pH is maintained in a range of about 6.0 to about 8.5, preferably 7.0 to 8.0. Control of the pH can be by monitoring of the system and an addition of appropriate pH adjusting materials to achieve this pH range.

The culturing is conducted basically under aerobic conditions of a dissolved oxygen concentration of about 2 ppm or more, preferably about 5 ppm or more. These conditions can be simply achieved in any manner conventional in the art and appropriate to the treatment system design being employed. For example, air can be bubbled into the system, the system can be agitated, a trickling system can be employed, etc.

The wastewater to be subjected to the process of this invention may contain sufficient nitrogen and phosphorus for culturing without the need for any additional source of nitrogen or phosphorus being added. However, in the event the wastewater is deficient in these two components, suitable available nitrogen sources, such as ammonia or an ammonium salt, e.g., ammonium sulfate, can be added to achieve an available nitrogen content of at least about 10 ppm or more per 100 $BOD_5$. Similarly, phosphorus can be supplemented, if necessary, by addition of orthophosphates, e.g., sodium phosphate, to achieve a phosphorus level in the wastewater of about 1 ppm or more per 100 $BOD_5$. In general, the treatment is conducted for a sufficient time to achieve the reduction in color desired and, in general, about 24 hours to about 8 weeks or longer, although this will depend upon the temperature of culturing, the liquor concentration and volume to be treated and other factors, has been found to be suitable.

In the above manner, difficultly degradable color bodies, as well as other organic compounds which might be present in such wastewater streams, can be advantageously treated to provide treated wastewater suitable for discharge after any additional conventional processing such as settling, chlorination, etc. into rivers and streams.

In order to further demonstrate the effectiveness of the strain of *Pseudomonas aeruginosa* 4-5-14, the following examples are given as exemplary of the invention but without intending to limit the same. Unless otherwise indicated herein, all parts, percents, ratios and the like are by weight.

EXAMPLE 1

A biotower, which basically was a trickling filter, was used. The biotower comprised a reservoir for a liquid and a column containing Pall rings of a plastic resin, with one end of the column being placed just above the liquid in the reservoir. A pump was submerged in the liquid reservoir for recycling liquid from the liquid reservoir through a tube to the top of the column for dispersion of the liquid down through the Pall ring packing. A slime layer of the *Pseudomonas aeruginosa* 4-5-14 was built up on the plastic ring media in the biotower by recycling a solution of 2% whey, 0.5% disodium phosphate and 0.1% $NH_4SO_4$ in water inoculated with *Pseudomonas aeruginosa* 4-5-14.

After the slime layer had been developed in the manner described above, the biotower liquid reservoir was filled with Kraft black liquor wastewater which had been fortified with nitrogen and phosphorus using ammonium sulfate and disodium phosphate, respectively, to a concentration of 400 mg/l and 80 mg/l, respectively, and the fortified Kraft black liquor wastewater was cycled from the reservoir therefor through the column and recirculated. Periodic samples were removed from the reservoir for color measurement.

Kraft black liquor wastewaters from two separate Kraft process mills were used employing the technique set forth above. One Kraft process wastewater (designated hereinafter as "Wastewater A") was a bleached "ceded" wastewater which was high in color. The second wastewater (designated hereinafter as "Wastewater B") was wastewater from an unbleached Kraft process, which was relatively low in color. The characteristics of these two Kraft process mill wastewaters are set forth in Table 7 below.

TABLE 7
CHARACTERIZATION OF KRAFT PROCESS WASTEWATERS

| SAMPLE LOCATION | pH | COLOR | BOD | COD |
|---|---|---|---|---|
| A. Industrial Site #1 | | | Bleached ceded | |
| Inflow ASB | 6.35 | 1780 | 250–300 | |
| Outflow ASB | 6.7 | 2090 | 30–60 | |
| Lagoon (Sample 1) | 6.9 | 2623 | | |
| (Sample 2) | 6.9 | 3942 | 20–40 | |
| B. Industrial Site #2 | | | Unbleached | |
| Mill Effluent | 7.5 | 590 | 500 | 6000 |

ASB = Aerated Stabilization Basin.

The wastewater was recycled through the biotower with a turn-over time of the batch volume through the biotower approximating twelve times per hour. The initial color of the wastewater was 3,423 units and a 30% reduction was observed during the first six hours of operation.

It was found that the color reduction was substantially linear over the six-hour period. The color reduction rate sharply decreased after the six-hour period, decreasing 16% more to a value of 1,848 color units during the next forty hours. In additional batch runs, an initial drop of 30% in color concentration of Wastewater A was obtained during the first four to seventeen hours and an additional drop of 16–24% with further recycling of Wastewater A.

Similar procedures were performed using Wastewater B. An approximately linear decrease in color over a period of 25 hours occurred for a total reduction of 54% to a value of 260 color units.

EXAMPLE 2

In this example, wastewater from a paper mill with different characteristics (designated hereinafter as "Wastewater C") was employed.

To evaluate the ability of the strain Pseudomonas aeruginosa 4-5-14 of this invention to decolorize such wastewater, two 1-liter Imhoff cones equipped with an air sparging stone at the bottom thereof were employed. The cones were filled with one liter of the Wastewater C and treated by sparging air through the Wastewater C at a moderate rate. No additional nutrients or substances were added during the course of the testing.

Two tests were conducted, one a control and the second using washed cells of Pseudomonas aeruginosa 4-5-14.

The washed cells of Psuedomonas aeruginosa 4-5-14 used above were prepared by soaking five grams of wheat bran containing Pseudomonas aeruginosa 4-5-14 in 150 ml of water over night. The supernatant was decanted and centrifuged at 10,500×G and the cell pellet obtained was resuspended in distilled water with any existing solids present settling out. The supernatant was decanted and centrifuged and the pellet was used to inoculate the wastewater employed.

The color of Wastewater C before and after treatment was analyzed by diluting 4 ml of Wastewater C in 10 ml of pH 7.6 phosphate buffer (14 ml in total). This diluted sample was mixed well and centrifuged at 10500×G for thirty minutes, which is equivalent to filtration through a 0.8 micron filter. The color of the supernatant obtained was read as percent transmission at 465 millimicrons blanked against a pH 7.6 phosphate buffer comprising 13 mls of a solution of 0.089 g/l $KH_2PO_4$ plus 86.8 mls of a solution of 11.889 g/l $Na_2HPO_4.2H_2O$. The color concentration was determined using the following relationship.

Color = (1.9960 − Log [% Transmission]) × (3626)

The results obtained in terms of time of treatment are set forth below, both for the control and the washed cells of Pseudomonas aeruginosa 4-5-14.

TABLE 8

| | COLOR | |
|---|---|---|
| HOURS RUN | CONTROL | WASHED CELLS |
| 0 | 790 | 790 |
| 24 | 780 | 469 |
| 72 | 654 | 349 |
| 96 | 681 | 445 |
| 144 | 645 | 422 |
| 264 | 648 | 417 |

The results obtained above demonstrate that the culture of Pseudomonas aeruginosa 4-5-14 was effective to remove color from Wastewater C. More specifically, the results show that the culture of Pseudomonas aeruginosa 4-5-14 was effective in removing 35% of the color from Wastewater C.

EXAMPLE 3

A sample of a wastewater from another paper company (designated hereinafter as "Wastewater D") was employed. 100 ml aliquots were placed in shake flasks and treated with 0.25 grams of Pseudomonas aeruginosa 4-5-14 culture. Culturing was conducted in the shake flask while shaking at a temperature of 20° C. for six days.

The following results were obtained.

TABLE 9

| SAMPLE | COD (mg/l) | COLOR (COLOR UNITS) |
|---|---|---|
| Untreated | 1365 | 1990 |
| Treated | 1068 | 1468 |
| % Reduction | 22% | 26% |

The above results demonstrate that the color value was reduced by a factor 26%.

From the above results, it can be seen that the strain Pseudomonas aeruginosa 4-5-14 of this invention can be effectively used in treating wastewater effluent from pulp and paper processes in an effective manner.

While the invention has been described in detail and with reference to specific embodiments thereof, it will be apparent to one skilled in the art that various modifications and changes may be made therein without departing from the spirit and scope thereof.

What is claimed is:

1. A biologically pure culture of the microorganism Pseudomonas aeruginosa having the identifying characteristics of ATCC 31482, said microorganism being capable upon culturing in pulp and paper mill wastewater of utilizing colorant substances in said wastewater as an assimilable source of carbon.

* * * * *